(12) United States Patent
Grasse et al.

(10) Patent No.: US 8,231,569 B2
(45) Date of Patent: Jul. 31, 2012

(54) TORQUE-LIMITING CATHETER HANDLE

(75) Inventors: Martin Maitre Grasse, Boston, MA (US); Anthony D. Hill, Minneapolis, MN (US); Don Curtis Deno, Andover, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

(21) Appl. No.: 12/968,149

(22) Filed: Dec. 14, 2010

(65) Prior Publication Data

US 2012/0150106 A1 Jun. 14, 2012

(51) Int. Cl.
*A61M 37/00* (2006.01)
*A61M 25/00* (2006.01)
*B25B 23/157* (2006.01)

(52) U.S. Cl. .................. 604/95.04; 604/523; 81/473

(58) Field of Classification Search ............... 604/95.04, 604/523, 524, 526, 527; D8/24; 81/467–483
See application file for complete search history.

(56) References Cited

U.S. PATENT DOCUMENTS

| | | | | |
|---|---|---|---|---|
| 4,878,405 A * | 11/1989 | Wolfe | | 81/57.31 |
| 4,892,337 A * | 1/1990 | Gunderson et al. | | 285/333 |
| 4,986,369 A * | 1/1991 | Fushiya et al. | | 173/178 |
| 5,094,133 A * | 3/1992 | Schreiber | | 81/474 |
| 5,496,139 A * | 3/1996 | Ghode et al. | | 409/182 |
| 5,823,702 A * | 10/1998 | Bynum | | 403/320 |
| 6,220,368 B1 * | 4/2001 | Ark et al. | | 173/178 |
| 6,257,351 B1 * | 7/2001 | Ark et al. | | 173/178 |
| 6,640,674 B1 * | 11/2003 | Rinner et al. | | 81/475 |
| 6,997,084 B1 * | 2/2006 | Gao et al. | | 81/62 |
| 7,032,931 B2 * | 4/2006 | Austin | | 285/92 |
| 7,048,711 B2 * | 5/2006 | Rosenman et al. | | 604/95.04 |
| 7,076,854 B2 * | 7/2006 | Harms et al. | | 29/507 |
| 7,334,509 B1 * | 2/2008 | Gao | | 81/475 |
| 7,494,158 B2 * | 2/2009 | Weh et al. | | 285/322 |
| 7,498,509 B2 * | 3/2009 | Brotzell et al. | | 174/21 R |
| 7,530,607 B2 * | 5/2009 | Luft | | 285/402 |
| 7,568,737 B2 * | 8/2009 | Wells et al. | | 285/391 |
| 7,762,164 B2 * | 7/2010 | Nino et al. | | 81/475 |
| 7,793,573 B2 * | 9/2010 | Gao | | 81/475 |
| 7,938,046 B2 * | 5/2011 | Nino et al. | | 81/475 |
| 2002/0008386 A1 * | 1/2002 | Lee | | 285/322 |
| 2004/0089106 A1 * | 5/2004 | Wolfe et al. | | 81/58.3 |
| 2004/0150223 A1 * | 8/2004 | Campau | | 285/308 |
| 2004/0164547 A1 * | 8/2004 | Cronley | | 285/34 |
| 2004/0216976 A1 * | 11/2004 | Droste | | 192/55.1 |
| 2006/0211534 A1 * | 9/2006 | Roberts et al. | | 475/317 |
| 2007/0144280 A1 * | 6/2007 | Bare | | 74/63 |
| 2010/0168717 A1 * | 7/2010 | Grasse et al. | | 604/524 |
| 2010/0251861 A1 * | 10/2010 | Sixto et al. | | 81/467 |

* cited by examiner

*Primary Examiner* — Victoria P Shumate
(74) *Attorney, Agent, or Firm* — Wiley Rein LLP

(57) ABSTRACT

A catheter includes a handle that advantageously limits the amount of torque that can be imparted to the body of the catheter. This advantageously reduces the likelihood of catheter failure, damage to tissue, or damage to medical devices introduced into the vasculature via the catheter. The catheter handle includes a grip portion that the practitioner manipulates in order to impart a torque and a torque transmitting portion operably coupled thereto that transmits the torque to the catheter body. A torque limiting mechanism decouples the torque transmitting portion from the grip portion, the body, and/or any pull wires when the torque imparted to the grip portion exceeds a torque threshold, thereby preventing excessive torques from being transmitted to the catheter body and/or pull wires. A practitioner may be able to adjust the torque threshold and may be able to disable the torque limiting mechanism.

17 Claims, 4 Drawing Sheets

TORQUE-LIMITING CATHETER HANDLE

BACKGROUND OF THE INVENTION a. Field of the Invention

The instant disclosure relates generally to catheters for use in the human body. More specifically, the disclosure relates to a catheter handle that reduces the risk of the failure of such catheters when subjected to torques.

b. Background Art

Catheters are used for an ever growing number of medical procedures. To name just a few examples, catheters are used for diagnostic, therapeutic, and ablative procedures. Typically, the physician manipulates the catheter through the patient's vasculature to the intended site, such as a site within the patient's heart. The catheter typically carries one or more electrodes or other diagnostic or therapeutic devices, which can be used for ablation, diagnosis, cardiac mapping, or the like.

Since the path a catheter must navigate within a patient is often long and tortuous, steering forces must be transmitted over relatively great distances. It is known, however, to utilize one or more pull wires, which are typically offset from the central longitudinal axis of the catheter and which can be attached to one or more pull rings proximate the distal end of the catheter shaft, to manipulate the distal end of the catheter. Often, these pull wires are embedded into the wall of the catheter (as opposed to, for example, routed through a lumen within the interior of the catheter).

It is also desirable for the catheter to transmit a torque applied at the proximal end to the distal end. It has been discovered, however, that the amount of torque that can be applied to a catheter is limited, particularly where the pull wires are embedded in the catheter wall. For example, if the catheter shaft has a strong bend in it and is also deflected (e.g., one or more of the embedded pull wires is under tension), it will be difficult to impart a torque to the catheter shaft. If an operator applies additional torque to the catheter handle in an effort to overcome this "lockup" in the shaft, there is a risk of catheter failure.

BRIEF SUMMARY OF THE INVENTION

It is therefore an object of the present disclosure to provide a catheter handle that limits the amount of torque that can be applied to the catheter shaft or body.

It is another object of the present disclosure to provide a catheter handle that has an adjustable threshold for the amount of torque that can be applied to the catheter shaft or body.

According to a first aspect of the present disclosure, a catheter includes: a catheter body having a proximal end; and a handle coupled to the proximal end of the catheter body such that a torque imparted to the handle can be transmitted to the catheter body. The handle includes: a grip portion adapted to be gripped in order to impart a torque; a torque transmitting portion operably coupled to the grip portion in order to transmit the torque imparted to the grip portion to the catheter body; and a torque limiting mechanism operable to decouple the torque transmitting portion and the grip portion when the torque imparted to the grip portion exceeds a torque threshold, such that torques in excess of the torque threshold are not transmitted to the catheter body.

In some embodiments, the torque limiting mechanism includes: a first torque transfer mating structure on the grip portion; and a second torque transfer mating structure that is complementary to the first torque transfer mating structure on the torque transmitting portion. When the torque imparted to the grip portion is less than the torque threshold, the first and second torque transfer mating structures remain engaged such that the torque imparted is transmitted to the catheter body. Conversely, when the torque imparted to the grip portion exceeds the torque threshold, the first and second torque transfer mating structures disengage such that the grip portion rotates relative to the torque transmitting portion, thereby preventing the torque imparted from being transmitted to the catheter body. The first and second torque transfer mating structures can be complementary ridged surfaces.

It is contemplated that the grip portion can include a longitudinally-extending bore, such that the torque transmitting portion can be disposed substantially concentrically with the grip portion within the longitudinally-extending bore thereof.

Optionally, the handle also includes a torque threshold adjustment structure. For example, a chuck, such as a collet positioned around the grip portion of the handle, can be provided to allow a practitioner to adjust the torque threshold.

It is contemplated that the torque limiting mechanism can be disengaged by the practitioner such that all torques imparted to the grip portion are transmitted to the catheter body. For example, the torque limiting mechanism can be disengaged by sliding the grip portion relative to the torque transmitting portion.

In another aspect of the disclosure, a catheter includes: a catheter body having a proximal end; and a handle coupled to the proximal end of the catheter body such that a torque imparted to the handle can be transmitted to the catheter body. The handle includes: a grip portion adapted to be gripped in order to impart a torque; a torque transmitting portion operably coupled to the grip portion and the catheter body in order to transmit the torque imparted to the grip portion to the catheter body; and a torque limiting mechanism operable to decouple the torque transmitting portion from at least one of the grip portion and the catheter body when the torque imparted to the grip portion exceeds a torque threshold so that torques in excess of the torque threshold are not transmitted to the catheter body. Thus, in some embodiments, the torque limiting mechanism decouples the torque transmitting portion and the grip portion when the torque imparted to the grip portion exceeds the torque threshold.

Optionally, the grip portion can be movable relative to the torque transmitting portion between a first position and a second position. When the grip portion is in the first position, the torque limiting mechanism is engaged such that torques in excess of the torque threshold are not transmitted to the catheter body, and, when the grip portion is in the second position, the torque limiting mechanism is disengaged such that all torques imparted to the grip portion are transmitted to the catheter body.

A collet can also be positioned around the grip portion of the handle such that tightening the collet increases the torque threshold and loosening the collet decreases the torque threshold.

The ordinary artisan will appreciate that a steerable catheter, such as a steerable introducer catheter, generally includes at least one pull wire extending from the handle through the catheter body. Thus, it is also within the spirit and scope of the present disclosure for the torque limiting mechanism to operate to prevent torques in excess of the torque threshold from being transmitted to the at least one pull wire. This advantageously reduces the likelihood of pull wire breakage.

In still another aspect of the present disclosure, a catheter includes: a catheter body having a proximal end; and a catheter handle coupled to the proximal end of the catheter body.

The catheter handle includes torque transmitting means for enabling torques below a torque threshold to be transmitted to the catheter body and for preventing torques above a torque threshold from being transmitted to the catheter body. Optionally, the catheter also includes means for adjusting the torque threshold and/or means for disengaging the torque transmitting means such that all torques are transmitted to the catheter body.

An advantage of the present disclosure is that it reduces the likelihood of catheter shaft failure by limiting the amount of torque that can be applied to the catheter shaft.

Another advantage of the present disclosure is that it provides for a variable threshold for the amount of torque that can be applied to the catheter or shaft body.

Still another advantage of the present disclosure is that it allows a user to elect to disable or disengage the torque-limiting feature.

The foregoing and other aspects, features, details, utilities, and advantages of the present disclosure will be apparent from reading the following description and claims, and from reviewing the accompanying drawings.

DETAILED DESCRIPTION OF THE INVENTION

The present disclosure provides a catheter handle that advantageously limits the amount of torque that can be imparted to the shaft (or "body") of the catheter, thereby reducing the likelihood of failure of the catheter body. For purposes of illustration, the disclosure will be described in connection with a steerable introducer catheter, such as the Agilis™ and Agilis™ NxT Steerable Introducer Catheters of St. Jude Medical, Atrial Fibrillation Division, Inc. It should be understood, however, that the principles disclosed herein could also be practiced to good advantage in other contexts, and are particularly advantageous in connection with catheters and other medical devices that include pull wires embedded in the catheter walls.

Figure 1:
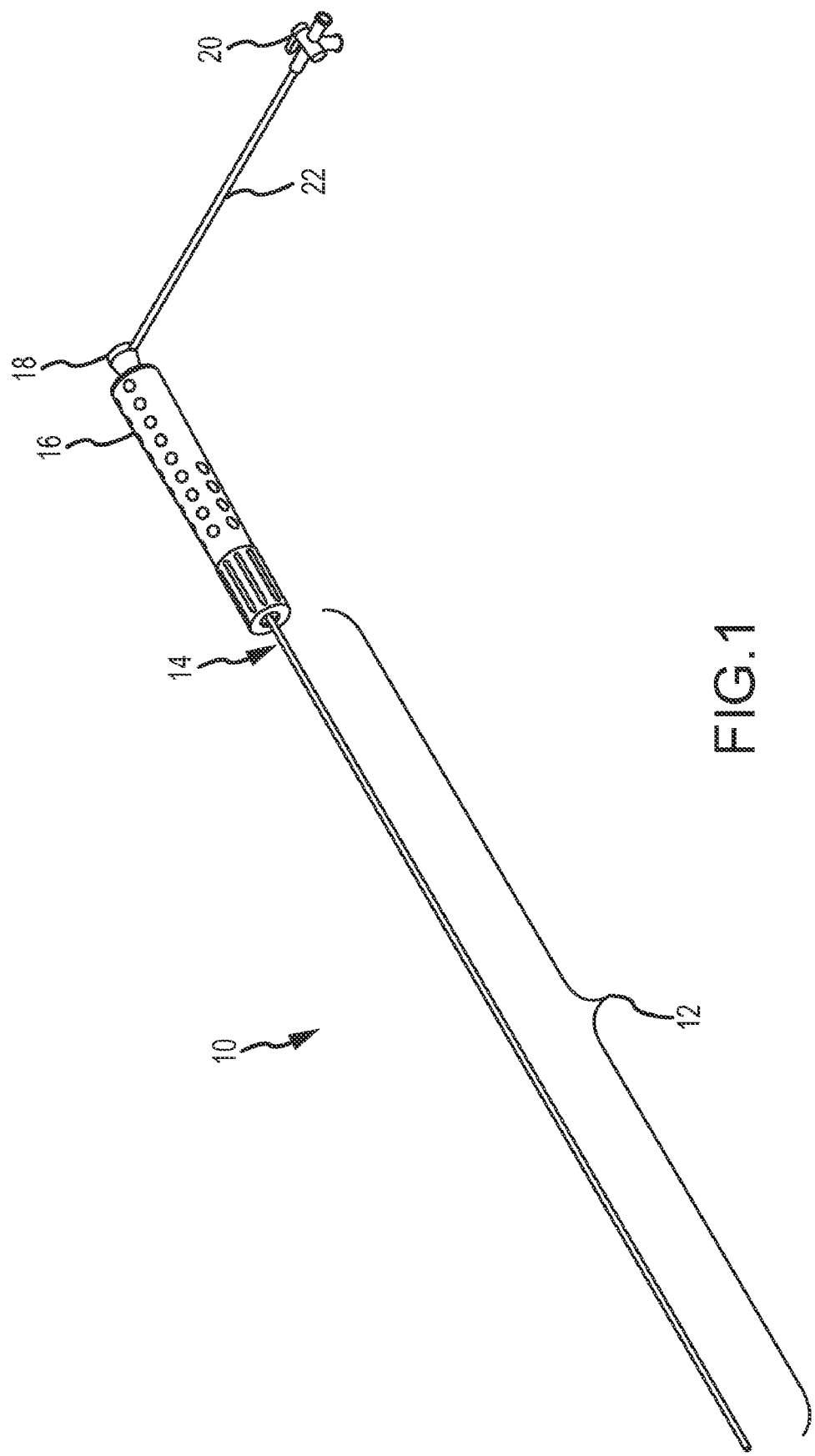
FIG. 1 is a perspective view of an embodiment of a catheter including a handle according to the present disclosure.

FIG. 1 is a perspective view of an exemplary steerable catheter 10. Catheter 10 includes an elongate catheter body 12 having a proximal end 14 and a handle 16 coupled to proximal end 14 of catheter body 12. Handle 16 is coupled such that a torque imparted to handle 16 can be transmitted to catheter body 12.

Catheter 10 can also include a hub 18 operably connected to an inner lumen within handle 16 for insertion or delivery of catheter assemblies, fluids, or any other devices known to those of ordinary skill in the art. Optionally, catheter 10 further includes a valve 20 operably connected to hub 18, such as via suitable tubing 22.

Figure 2:
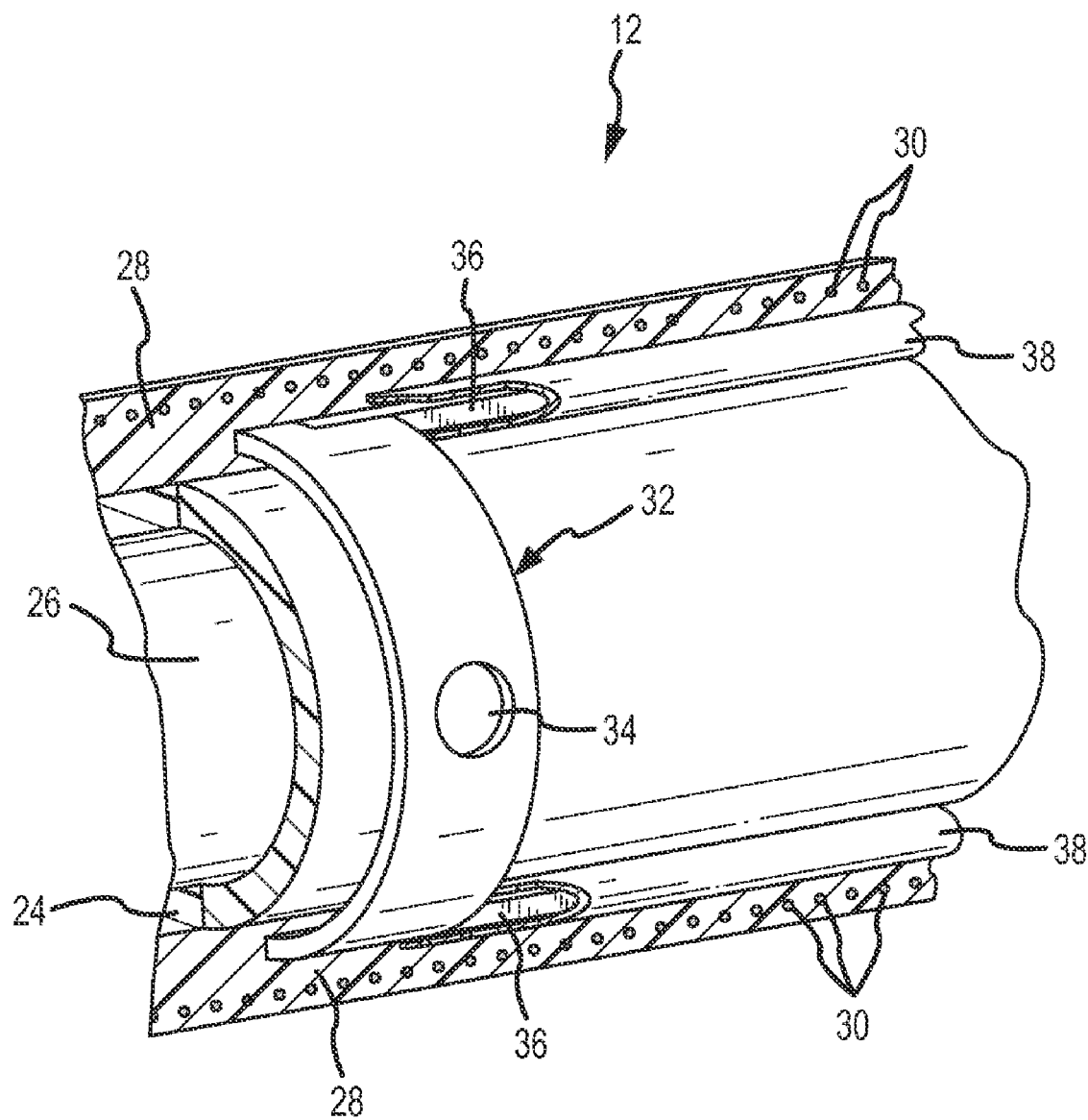
FIG. 2 illustrates a perspective view of a section of a steerable catheter, cut away to show details.

FIG. 2 is a perspective view of one embodiment of catheter body 12 such as can be employed in connection with the present disclosure. The details of construction of catheter body 12 will be generally familiar to those of ordinary skill in the art and therefore need not be described in detail herein. Briefly, however, FIG. 2 depicts a multi-layer construction including an inner layer 24 defining a central lumen 26 and an outer layer 28 including a wire reinforcing layer 30. Also depicted are a pull ring 32 including a flow hole 34 to facilitate bonding of pull ring 32 into catheter body 12. Two pull wires 36 are coupled to pull ring 32 in order to deflect catheter body 12 as generally known in the art. Though pull wires 36 are depicted as encased in so-called "spaghetti tubes" 38, it should be understood that they could alternatively be embedded directly in either inner layer 24 or outer layer 28 (that is, spaghetti tubes 38 could be omitted without altering the principles of the disclosure as described herein).

Figure 3:
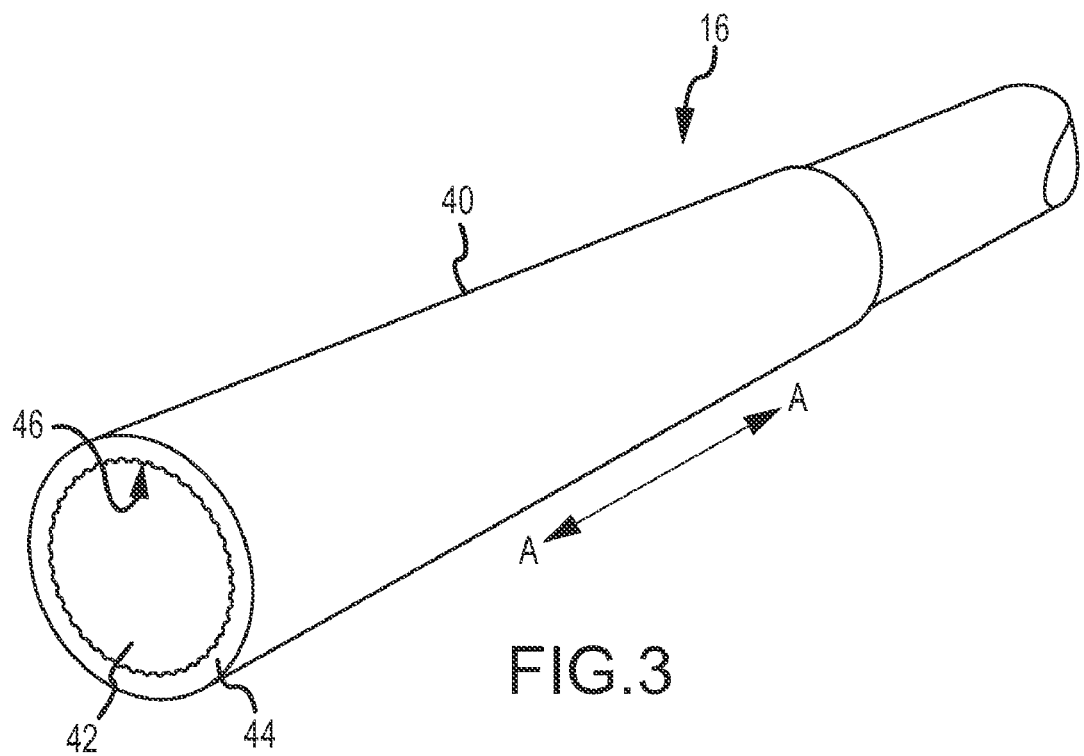
FIG. 3 is a schematic perspective illustration of a catheter handle according to an embodiment of the present disclosure.
Figure 4:
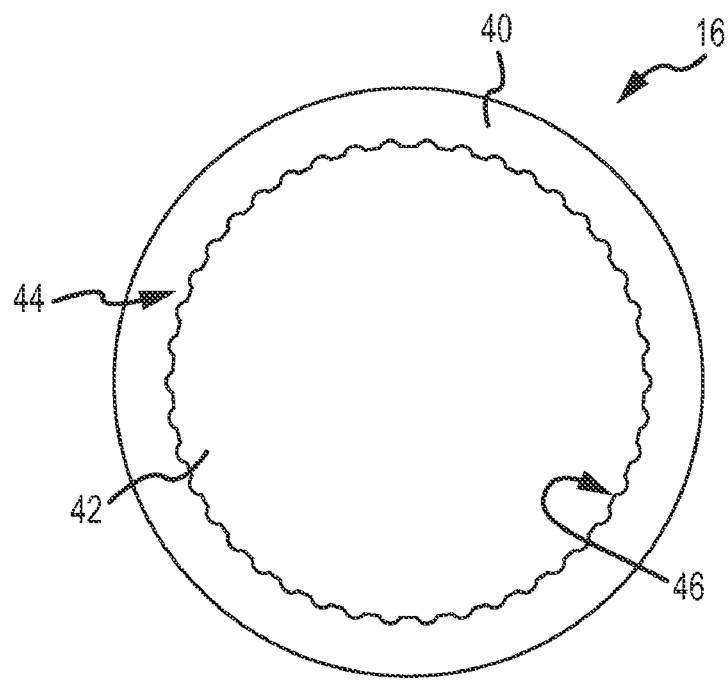
FIG. 4 is an end view of the catheter handle depicted in FIG. 3.
Figure 5:
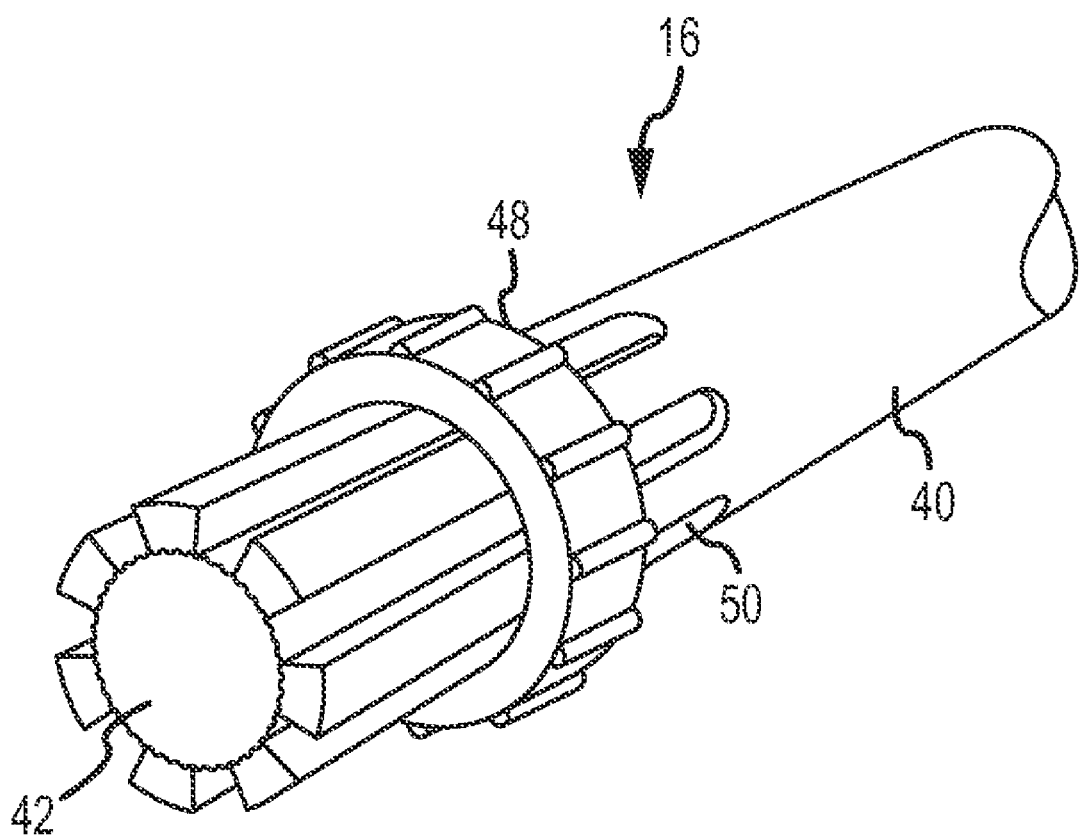
FIG. 5 illustrates a handle according to the present disclosure including a collet to adjust the torque threshold.

Additional aspects of the present disclosure will now be described with reference to FIGS. 3 through 5. FIG. 3 is a schematic perspective illustration of handle 16 according to one embodiment. FIG. 4 is a schematic end view of handle 16 according to the same embodiment of the present disclosure.

One of ordinary skill in the art will be generally familiar with conventional handle design for steerable catheters, including the use of various actuators and mechanisms to effect deflection of the distal end of catheter body 12. Accordingly, handle 16 will only be described herein to the extent necessary to understand the present disclosure.

As seen in FIGS. 3 and 4, handle 16 generally includes two components: a grip portion 40 and a torque transmitting portion 42. Grip portion 40 is adapted to be gripped (e.g., manually by a user or within a robotic control system) in order to impart a torque to handle 16. Torque transmitting portion 42 is operably coupled to both grip portion 40 and catheter body 12 such that a torque imparted to grip portion 40 can be transmitted through torque transmitting portion 42 to catheter body 12.

As shown in FIGS. 3 and 4, in some embodiments, grip portion 40 includes a longitudinally-extending bore within which torque transmitting portion 42 is disposed. Typically, grip portion 40 and torque transmitting portion 42 are substantially concentric—that is, their central longitudinal axes are generally coincident.

Handle 16 further includes a torque limiting mechanism. The torque limiting mechanism operates to decouple torque transmitting portion 42 from grip portion 40 and/or catheter body 12 when the torque imparted to grip portion 40 exceeds a torque threshold. Advantageously, therefore, the torque limiting mechanism prevents torques that might cause catheter body 12 to fail from being transmitted to catheter body 12.

FIGS. 3 and 4 depict one embodiment of a torque limiting mechanism according to the present disclosure. As illustrated in FIGS. 3 and 4, grip portion 40 includes a first torque transfer mating structure 44 and torque transmitting portion 42 includes a second torque transfer mating structure 46. First and second torque transfer mating structures 44, 46 are typically complementary to each other. That is, convex shapes in one of the structures mate with concave shapes in the other and vice-versa. In the embodiment shown in FIGS. 3 and 4, first and second torque transfer mating structures 44, 46 are ridged surfaces, such as oval-shaped, geartooth-like, or sawtooth-like surfaces.

It should be understood, of course, that other configurations of torque transfer mating structures 44, 46 are contemplated. For example, a clutch mechanism, such as that employed in a click-type torque wrench, could also be used.

Torque transfer mating structures 44, 46 are configured such that, below a torque threshold, torque transfer mating structures 44, 46 remain engaged such that, when a torque is imparted to grip portion 40, the torque is transferred through torque transfer mating structures 44, 46 to torque transmitting portion 42, and in turn to catheter body 12. Torque transfer mating structures 44, 46 are further configured such that, if the torque imparted to grip portion 40 exceeds the torque threshold, torque transfer mating structures 44, 46 disengage, such that grip portion 40 "slips" relative to torque transmitting portion 42, thereby preventing these larger, potentially damaging torques from being transmitted through torque transmitting portion 42 to catheter body 12.

It should be understood that the torques imparted to grip portion 40 are also generally imparted to pull wires 36. Thus, it can also be desirable to decouple grip portion 40 from pull wires 36 above a torque threshold to avoid, for example, breaking pull wires 36 via the application of excessive torques.

One of ordinary skill in the art will appreciate how to design torque transfer structures 44, 46 for a particular torque threshold (e.g., by applying principles of machine design, torque transfer structures 44, 46 can be designed to "slip" at a particular torque). For example, one could determine the torque at which catheter body 12 is likely to fail, select an appropriate safety factor, calculate the resultant torque threshold, and then apply design principles to configure torque transfer structures 44, 46 to "slip" at this calculated torque threshold.

It is also contemplated that handle 16 can further include a torque threshold adjustment structure that permits the torque threshold to be adjusted by a user of catheter 10. For example, as shown in FIG. 5, a collet 48 can be positioned around grip portion 40, such as near the proximal end of handle 16. As one of ordinary skill in the art will appreciate from this disclosure, tightening collet 48 will increase the torque threshold (e.g., make it harder for grip portion 40 to slip relative to torque transmitting portion 42), while loosening collet 48 will decrease the torque threshold (e.g., make it easier for grip portion 40 to slip relative to torque transmitting portion 42). To facilitate this action, grip portion 40 can include slots 50 to allow grip portion 40 to change dimensions as collet 48 is tightened and loosened.

It can also be desirable in certain applications of catheter 10 to enable the user to disable the torque limiting features of handle 16. Accordingly, in some embodiments of the disclosure, grip portion 40 can be movable (for example, slideable along arrow A in FIG. 3) relative to torque transmitting portion 42 between a first position and a second position. In the first position, the torque limiting mechanism is engaged, for example as shown in FIGS. 3 and 4. In the second position, the torque limiting mechanism is disengaged, such that all torques imparted to grip portion 40, regardless of magnitude, are transmitted to catheter body 12.

This can be accomplished, for example, by tapering the ridged surfaces shown in FIGS. 3 and 4 appropriately. Such a configuration also offers another method of varying the torque threshold. That is, when grip portion 40 is in the first position, the torque threshold is at its minimum, and, as the user slides grip portion 40 towards the second position, the torque threshold increases until it reaches its maximum when grip portion 40 reaches the second position. Of course, one can also effectively disable the torque limiting features of handle 16 by further tightening collet 48, shown in FIG. 5, to such a degree that the torque threshold is above any torque that might be imparted to grip portion 40.

Although several embodiments of this disclosure have been described above with a certain degree of particularity, those skilled in the art could make numerous alterations to the disclosed embodiments without departing from the spirit or scope of this disclosure. For example although the disclosure has been described as having torque transmitting portion 42 disposed within grip portion 40, such that torque transfer mating structures 44, 46 are disposed on the inner and outer surfaces thereof, it is contemplated that grip portion 40 and torque transmitting portion 42 could be arranged abutting each other, with torque transfer mating structures 44, 46 on the abutting end faces thereof.

It should also be understood that an additional advantage of the present disclosure is that, by limiting the force applied to soft tissue adjacent catheter 10, the risk of tissue injury (e.g., puncture) can be reduced.

Similarly, steerable introducer catheters are often used to introduce medical devices with sensitive and/or delicate components, such as the piezoelectric crystals used in intracardiac echocardiography ("ICE") catheters. Excessive torques applied to the introduce catheter can damage such devices; the present disclosure addresses this concern as well.

All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure can be made without departing from the spirit of the disclosure as defined in the appended claims.

The invention claimed is:

1. A catheter comprising:
   a catheter body having a proximal end; and
   a handle coupled to the proximal end of the catheter body such that a torque imparted to the handle can be transmitted to the catheter body, the handle comprising:
      a grip portion adapted to be gripped in order to impart a torque;
      a torque transmitting portion operably coupled to the grip portion in order to transmit the torque imparted to the grip portion to the catheter body; and
      a torque limiting mechanism operable to decouple the torque transmitting portion and the grip portion when the torque imparted to the exterior of the grip portion exceeds a torque threshold, such that torques in excess of the torque threshold are not transmitted to the catheter body.

2. The catheter according to claim 1, wherein the torque limiting mechanism comprises:
   a first torque transfer mating structure on the grip portion; and
   a second torque transfer mating structure that is complementary to the first torque transfer mating structure on the torque transmitting portion,
   wherein, when the torque imparted to the grip portion is less than the torque threshold, the first and second torque transfer mating structures remain engaged such that the torque imparted is transmitted to the catheter body, and
   wherein, when the torque imparted to the grip portion exceeds the torque threshold, the first and second torque transfer mating structures disengage such that the grip portion rotates relative to the torque transmitting portion, thereby preventing the torque imparted from being transmitted to the catheter body.

3. The catheter according to claim 2, wherein the first and second torque transfer mating structures comprise ridged surfaces.

4. The catheter according to claim 1, wherein the grip portion includes a longitudinally-extending bore and the torque transmitting portion is disposed substantially concentrically with the grip portion within the longitudinally-extending bore thereof.

5. The catheter according to claim 1, wherein the handle further comprises a torque threshold adjustment structure.

6. The catheter according to claim 5, wherein the torque threshold adjustment structure comprises a chuck.

7. The catheter according to claim 6, wherein the torque threshold adjustment structure comprises a collet positioned around the grip portion of the handle.

8. The catheter according to claim 1, wherein the torque limiting mechanism can be disengaged such that all torques imparted to the grip portion are transmitted to the catheter body.

9. The catheter according to claim 8, wherein the torque limiting mechanism is disengaged by sliding the grip portion relative to the torque transmitting portion.

10. A catheter comprising:
a catheter body having a proximal end; and
a handle coupled to the proximal end of the catheter body such that a torque imparted to the handle can be transmitted to the catheter body, the handle comprising:
a grip portion adapted to be gripped in order to impart a torque;
a torque transmitting portion operably coupled to the grip portion and the catheter body in order to transmit the torque imparted to the grip portion to the catheter body; and
a torque limiting mechanism operable to decouple the torque transmitting portion from at least one of the grip portion and the catheter body when the torque imparted to the exterior of the grip portion exceeds a torque threshold so that torques in excess of the torque threshold are not transmitted to the catheter body.

11. The catheter according to claim 10, wherein
the grip portion is movable relative to the torque transmitting portion between a first position and a second position,
when the grip portion is in the first position, the torque limiting mechanism is engaged such that torques in excess of the torque threshold are not transmitted to the catheter body, and
when the grip portion is in the second position, the torque limiting mechanism is disengaged such that all torques imparted to the grip portion are transmitted to the catheter body.

12. The catheter according to claim 10, further comprising a collet positioned around the grip portion of the handle such that tightening the collet increases the torque threshold and loosening the collet decreases the torque threshold.

13. The catheter according to claim 10, wherein the torque limiting mechanism comprises complementary ridged surfaces on each of the grip portion and the torque transmitting portion.

14. The catheter according to claim 10, further comprising at least one pull wire extending from the handle through the catheter body, and wherein the torque limiting mechanism is operable to prevent torques in excess of the torque threshold from being transmitted to the at least one pull wire.

15. A catheter comprising:
a catheter body having a proximal end; and
a catheter handle coupled to the proximal end of the catheter body, the catheter handle comprising torque transmitting means for enabling torques applied to the exterior of the handle below a torque threshold to be transmitted to the catheter body and for preventing torques applied to the exterior of the handle above a torque threshold from being transmitted to the catheter body.

16. The catheter according to claim 15, further comprising means for adjusting the torque threshold.

17. The catheter according to claim 15, further comprising means for disengaging the torque transmitting means such that all torques are transmitted to the catheter body.

* * * * *